(12) United States Patent
Lee et al.

(10) Patent No.: US 6,217,553 B1
(45) Date of Patent: Apr. 17, 2001

(54) LIQUID MEDICINE-PRESCRIBING APPARATUS FOR BLOOD VESSEL INJECTION

(75) Inventors: Jong Woo Lee; Yong Suk Oh, both of Seoul (KR)

(73) Assignee: Ace Medical Co., Ltd., Seoul (KR)

( * ) Notice: Subject to any disclaimer, the term of this patent is extended or adjusted under 35 U.S.C. 154(b) by 0 days.

(21) Appl. No.: 09/272,252

(22) Filed: Mar. 19, 1999

(30) Foreign Application Priority Data

Nov. 19, 1998 (KR) .................................................. 98-49635

(51) Int. Cl.[7] .................................................. A61M 37/00
(52) U.S. Cl. .............................. 604/151; 604/65; 604/66
(58) Field of Search .............................. 604/65–67, 131, 604/151, 245, 246, 153

(56) References Cited

U.S. PATENT DOCUMENTS 5,482,446 * 1/1996 Williamson et al. ................ 417/474

* cited by examiner

Primary Examiner—John D. Yasko
(74) Attorney, Agent, or Firm—McGuireWoods, LLP

(57) ABSTRACT

A liquid medicine-prescribing apparatus for a blood vessel injection comprising a lowercase 10 which is combined with two lateral faces 10a, 10b, a running part 60 which has the feed means of liquid medicine and which is inserted into a reception space 24 formed by a cover plate 20 which is open and shut by a hinge 300 of lowercase 10 so that mounting and separation may be done, and an uppercase 30 which is open and shut by a hinge 21 of a cover plate 20, and on which the lowercase 10 is combined to be open and shut by forming the reception space 33 which receives liquid medicine pack. Also the liquid medicine-prescribing control circuit, wherein, with a central processing unit having a reference value according to each step, divided are a normal conversion switch NOR SW for normal operation, a switch INJ SW by which a personal conversion switch PCA MODE SW determines prescribing amount by changed value according to each step, a switch TM SW which determines prescribing time; and connection is provided through an AND gate; a safety node LOCK SW for prohibiting a personal conversion switch from being operated is connected into an input edge; a detector, with which state of a battery can be detected at any tames connected into a control part and, in case that a detected signal value is different from a set value which is already fixed, a motor control M/C, which control a motor operated simultaneously by a battery power and a buzzer which outputs buzzer sound in order to inform outside of state, is connected with a battery.

24 Claims, 17 Drawing Sheets

LIQUID MEDICINE-PRESCRIBING APPARATUS FOR BLOOD VESSEL INJECTION

BACKGROUND OF THE INVENTION

1. Field of the Invention

This invention relates to a liquid medicine-prescribing apparatus for blood vessel injection. The present invention provides a fixed quantity of liquid medicine which can be prescribed without a bottle or a pack being placed at an upper position. The present invention also presents a constant quantity of liquid medicine to be prescribed at the time of blood vessel injection. The present invention is also directed to a control system for prescribing liquid medicine and a liquid medicine-prescribing system which can be used for a disposable purpose such as a small portable system which has replaceable parts.

2. Discussion of Related Art

Generally speaking, in the case of a liquid medicine, prescribing apparatus for blood vessel injection, a liquid medicine bottle is hung at an upper position and a liquid medicine is input into a blood vessel through a liquid medicine hose. However, using such a system, when a patient moves, a liquid medicine bottle also is required to move simultaneously. Also, when the liquid medicine bottle is hung on the upper position, portability is comprised. Also, using such a system causes inconvenience because the liquid medicine can be used only in a fixed place.

Accordingly, recently a device, which is designed for easily carrying as well as for being injected without placing a liquid medicine bottle at an upper position, has been developed. However, most of these devices use a method which uses a silicon tube, through which a liquid medicine is supplied by expansion pressure while a tube is being expanded, so a liquid medicine is input into the tube. These devices may also use a method which uses electric power using an adapter and a battery. In these latter devices a liquid medicine can be input into a liquid medicine hose while a multiple axis, which circulates a curved surface and moves sequentially along a curved surface, pressurizes sequentially a liquid medicine hose and inputs a liquid medicine. However, the disadvantage of the method which uses a tube is that there is some difference in prescribing a liquid medicine, since the beginning pressure of a tube which swelled differs from the last pressure of that tube. In the case of the method where a multiple axis moves sequentially by a curved surface, there are disadvantages in that it is impossible to repair the device due to the complexity of manufacturing process, and because of high cost it is impossible to use it for a disposable purpose.

SUMMARY OF THE INVENTION

Accordingly, in order to overcome such drawbacks in the conventional art, it is therefore an object of the present invention to provide a liquid medicine-prescribing apparatus for blood vessel injection, wherein a driving part, in which a motor controlled properly at the control system is accepted while being driven by an electric power of a battery, is designed to be mounted and separated by being accepted into a case. If a driving roller is rotated, a pressurized roller, which is formed on a driving roller, pressurizes a pressurized hose sequentially, which is wound at the outside of the driving roller in the driving part which can be turned on and off by the staring part of the driving part, at the state that is pressurized by a starting part, so a fixed quantity of liquid medicine can be prescribed. This kind of supply method increases the liquid medicine by proper control within a fixed time or the electric power of a battery is designed to be maintained for a long time in turning a motor on and off and prescribing a fixed quantity.

It is another object to provide the liquid medicine-prescribing apparatus for blood vessel injection wherein a fixed quantity of liquid medicine can be prescribed without a bottle or a pack being placed at an upper position, which includes liquid medicine, while a constant quantity of liquid medicine is being prescribed at the time of blood vessel injection.

It is still another object to provide a control system for prescribing liquid medicine and a liquid medicine-prescribing system which can be used for a disposable purpose like a small portable system and which can replace parts easily.

To achieve these and other advantages and in accordance with the purpose of the present invention, there is provided a liquid medicine-prescribing apparatus for blood vessel injection comprising the lowercase 10 which is combined with two lateral faces 10a, 10b, the running part 60 which has feed the means of liquid medicine and which is inserted to be mounted and removed into the reception space 24 formed by the cover plate 20 which is open and shut by the hinge 300 of lowercase 10 and an uppercase 30 which is open and shut by the hinge 21 of a cover plate 20 and on which the lowercase 10 is combined to be open and shut while forming the reception space 33 into which liquid medicine pack is accepted.

According to another aspect of the present invention, there is also provided a liquid medicine-prescribing control circuit, wherein, with a central processing unit having a reference value according to each step, divided are a normal conversion switch NOR SW for normal operation, a switch INJ SW by which a personal conversion switch PCA MODE SW determines prescribing amount by changed value according to each step, and a switch TM SW which determines prescribing time and connection is provided through an AND gate. A safety node LOCK SW for prohibiting a personal conversion switch from being operated is connected into an input edge. A detector, with which state of a battery can be detected at any time, is connected into a control part and, in case that a detected signal value is different from a set value which is already fixed, a motor control M/C, which controls the motor operated simultaneously by battery power and the buzzer which outputs a buzzer sound in order to inform outside of state, is connected with a battery.

According to another aspect of the present invention, there is also provided a liquid medicine-prescribing system comprising a step which halts all operation, in the case that, in order to make the motor to be rotated by the operation of the normal conversion switch and the personal conversion switch, the new input state waits and the battery is not enough to meet the reference value by determining whether the battery capacity is proper or not, a step which determines whether the personal conversion switch, with which the patient can increase prescribing amount of liquid medicine additionally when capacity of it is proper, had already been operated. That is, a step which determines whether it is PCA mode, a step which makes additional operation to be possible at the state that PCA mode is already input in the case that it is not required to clear it, and which determines whether existing input PCA mode should be cleared in case that it is set in PCA mode. Also provided is a step which has PCA mode, which is input already, cleared in case that it is required to clear, a step which is immediately in normal operation if a safety pin has been removed by confirming whether a safety pin was removed(or not) (by confirming whether a safety switch is OFF (or not) in order for a patient to make it impossible to increase liquid medicine at his discretion in case that PCA mode has been cleared), a step which provides normal operation according to a reference value, in case that a reference value for normal operation has not been changed after determining whether it is changed or not, by determining whether PCA switch starts working newly when a safety pin has not been removed when PCA switch did not work (when a personal conversion switch and a time switch did not provide the increase of capacity and time simultaneously or turned OFF), a step which works normally by a changed reference value by a normal conversion switch in case that a normal conversion switch is changed by a reference value, and a step which works in additional operation as well as normal operation under PCA mode, if an additional operation is performed by a changed value immediately after PCA mode value is input according to a changed value, in case that P.A. switch has turned ON, that is to say, in case that a personal conversion switch, a switch which determines prescribing amount and a switch which determines prescribing time has increased together.

BRIEF DESCRIPTION OF THE ATTACHED DRAWINGS

A more complete appreciation of the invention, and many of the attendant advantages thereof, will be readily apparent as the same becomes better understood by reference to the following detailed description when considered in conjunction with the accompanying drawings in which like reference symbols represent the same or similar components, wherein.

DETAILED DESCRIPTION OF PREFERRED EMBODIMENT

From the following, a desirable embodiment of this invention will be described in detail according to the attached drawings.

Figure 1:
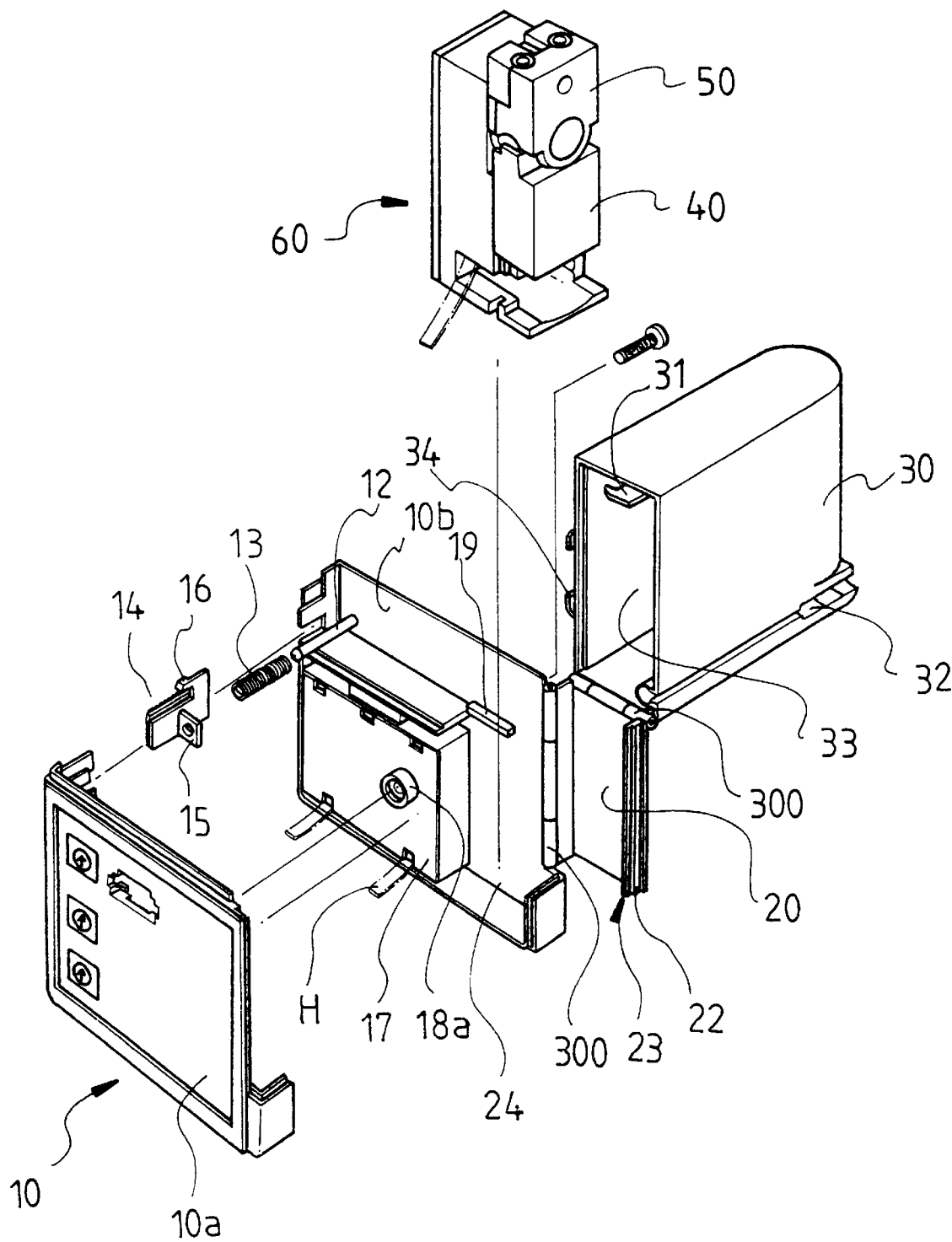
FIG. 1 is a perspective view showing a state, wherein a lowercase and an uppercase are open and shut by a hinge.
Figure 4:
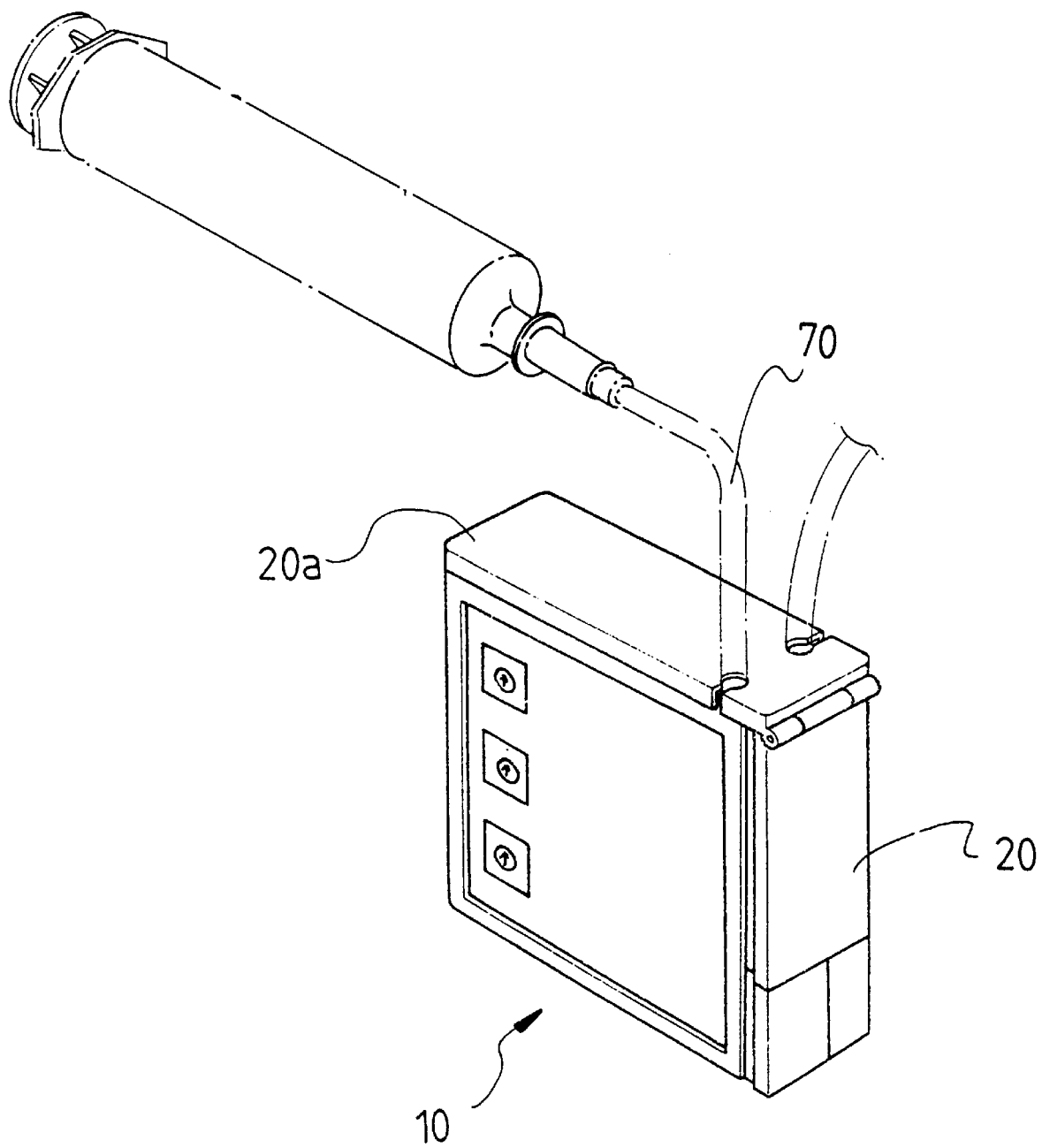
FIG. 4 is a perspective view showing a state, wherein an injector is connected without the uppercase.
Figure 6:
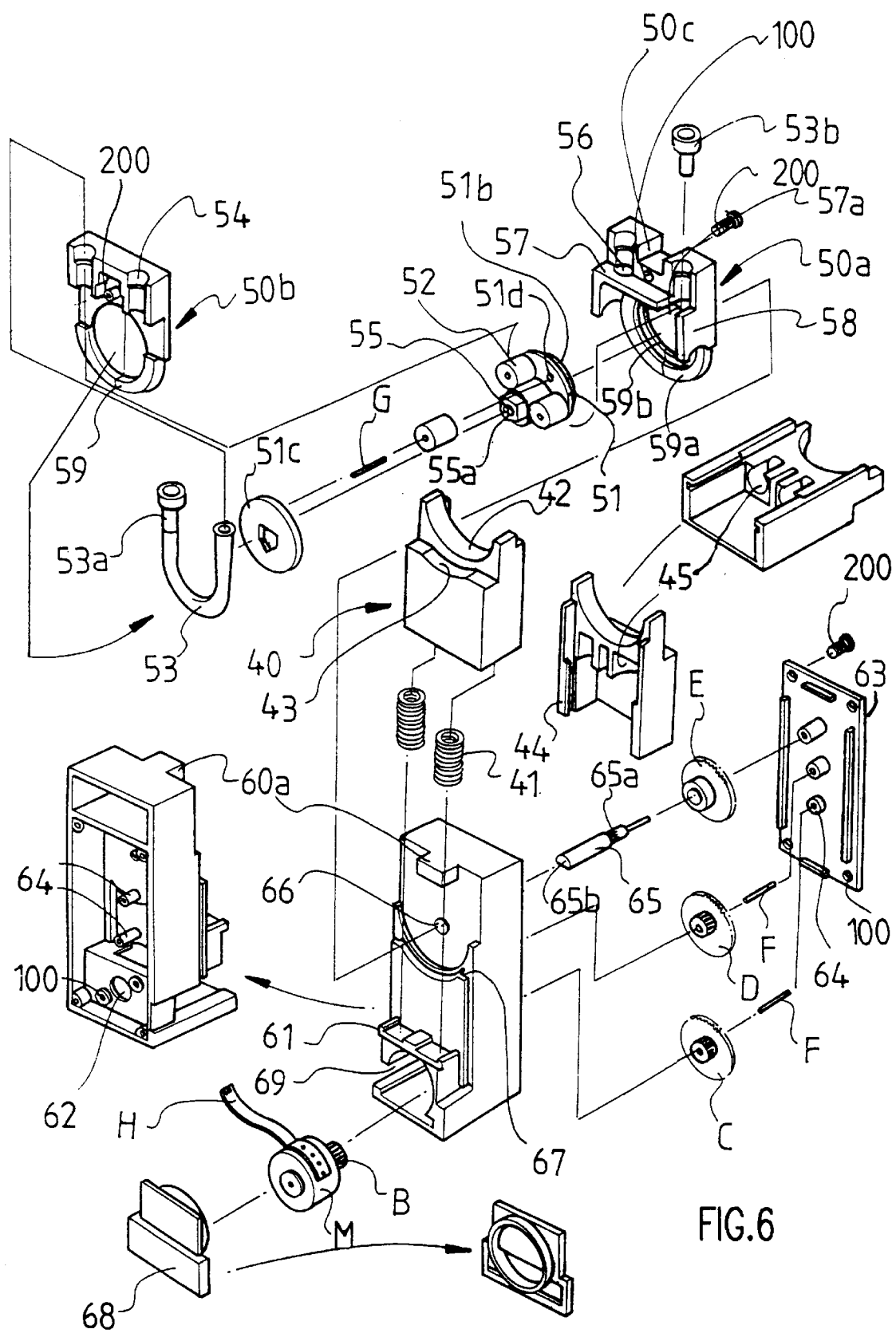
FIG. 6 is a disassembled perspective view showing the combined configuration of a driving part.
Figure 7:
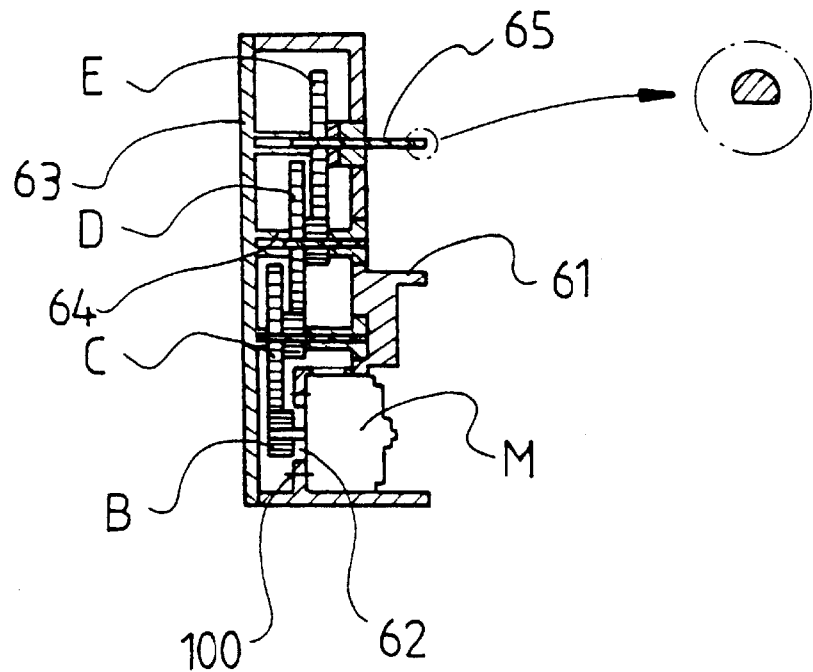
FIG. 7 is a cross sectional view showing a state, wherein a motor of a driving part is combined with a gear.
Figure 8:
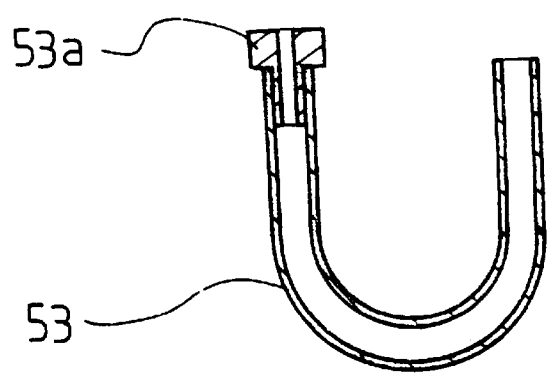
FIG. 8 is a cross sectional view showing a state, wherein a connector is combined with a pressurized hose.
Figure 9:
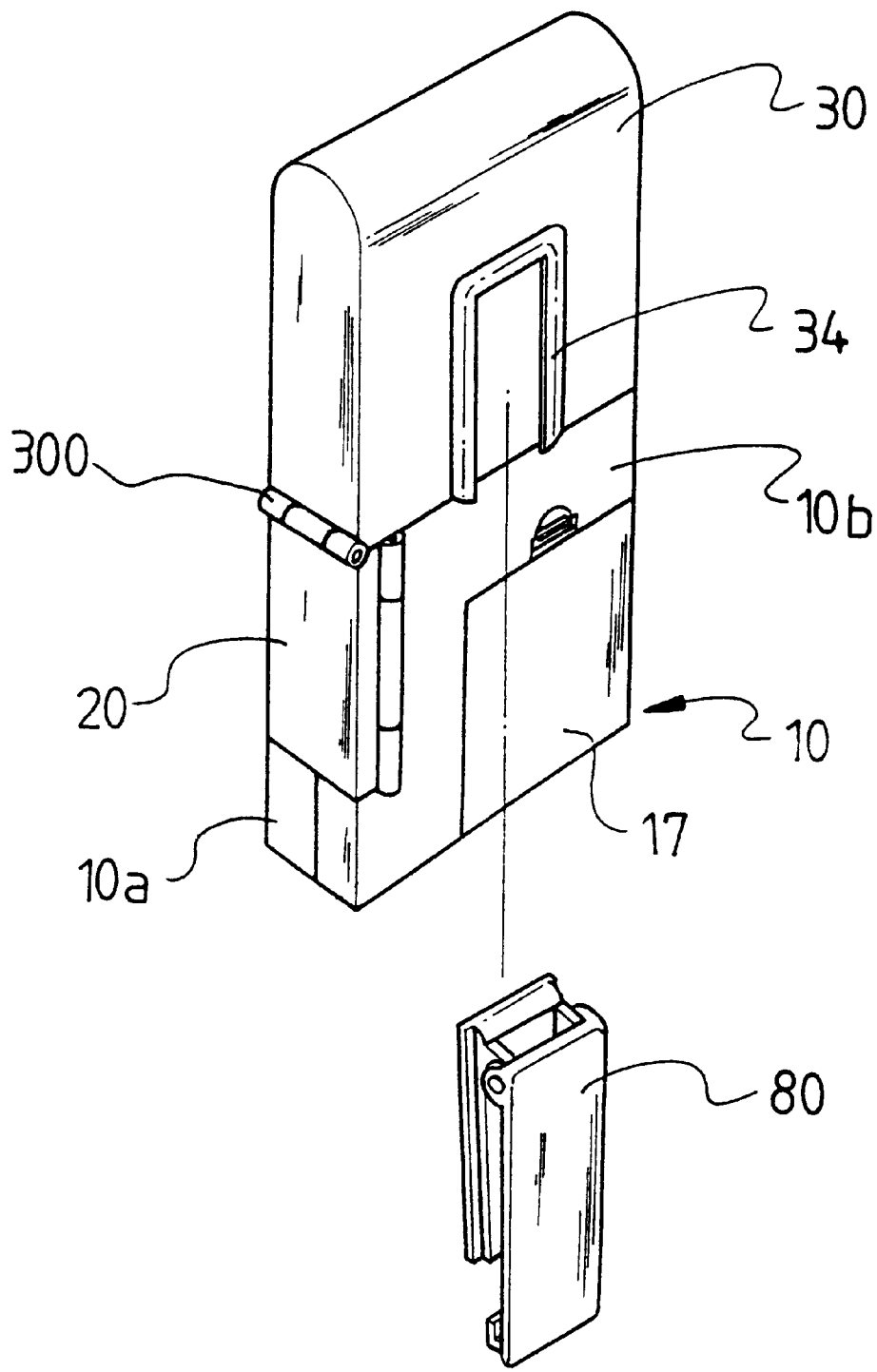
FIG. 9 is a partially disassembled perspective view showing a state, wherein a clip is connected to the uppercase.
Figure 10:
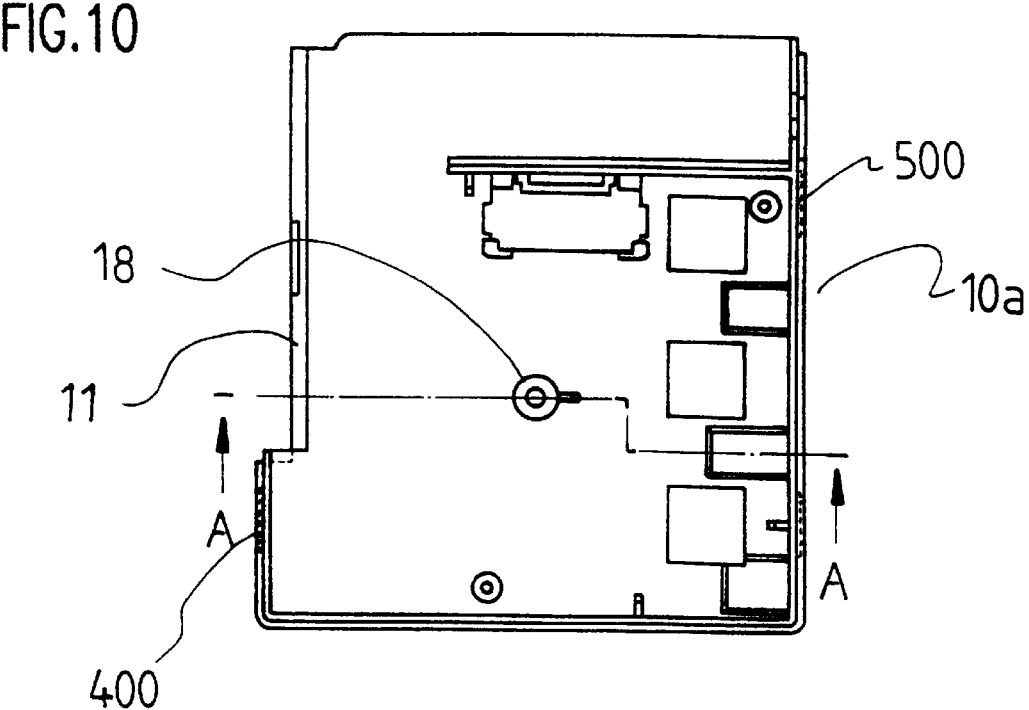
FIG. 10 is a front view showing a side of the lowercase in FIG. 1.
Figure 11:
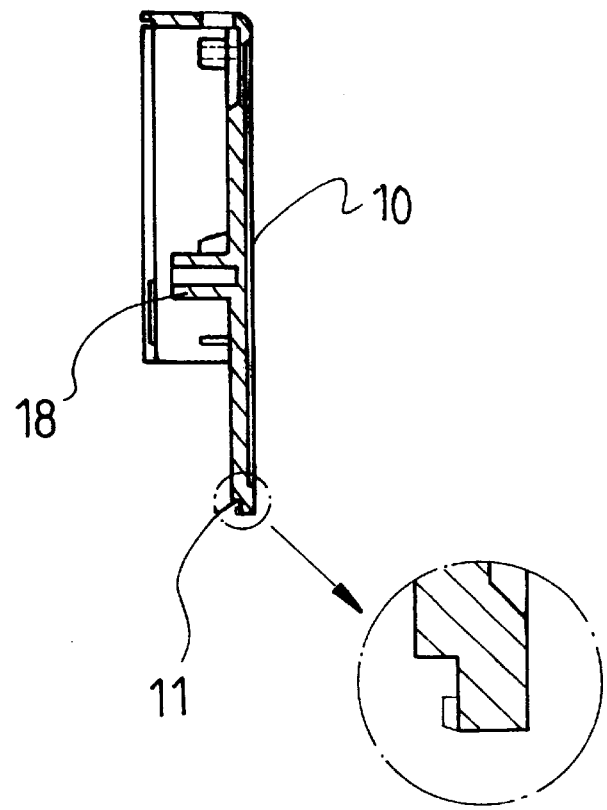
FIG. 11 is a cross sectional view taken along the line A—A in FIG. 10.
Figure 15:
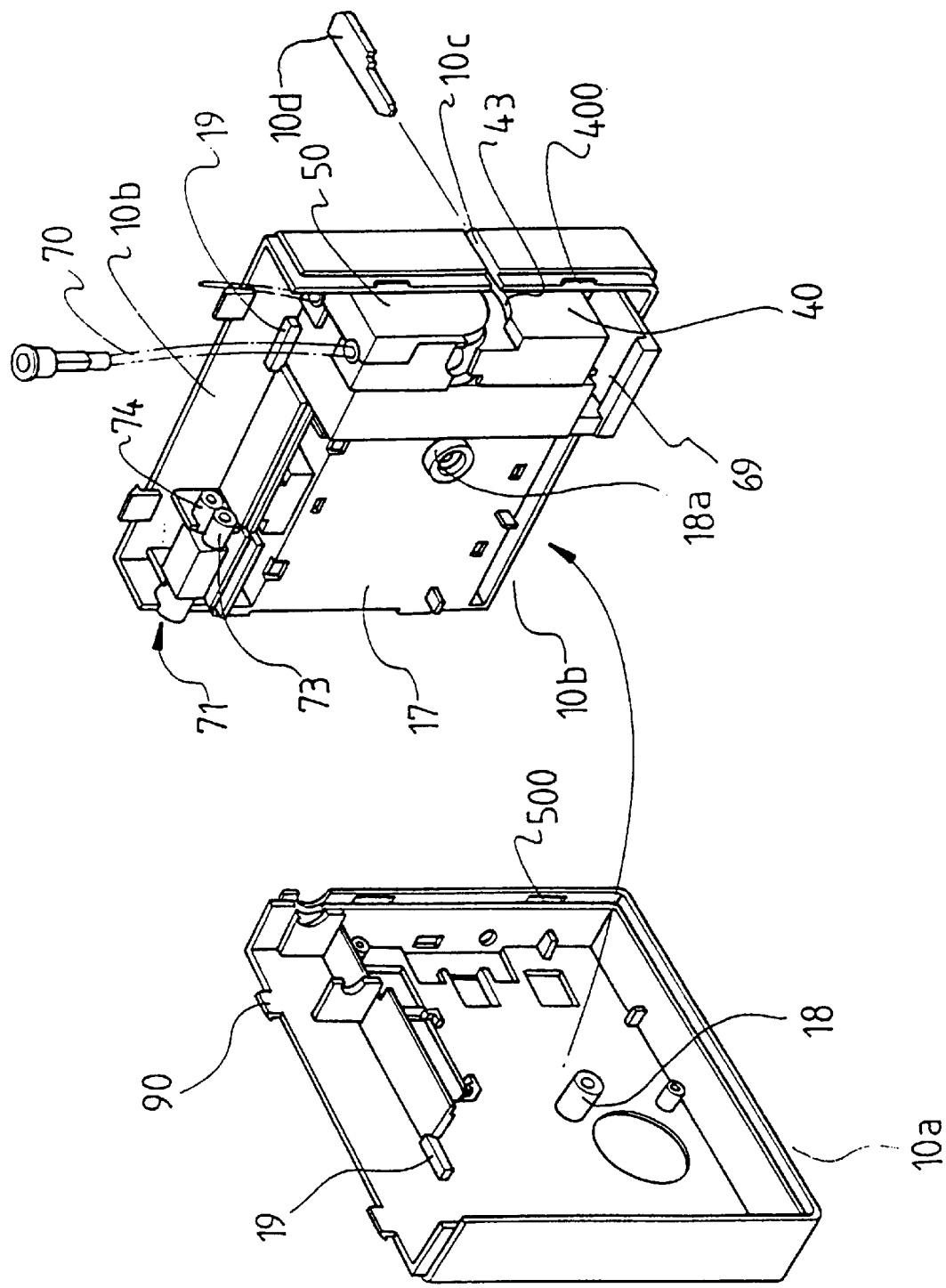
FIG. 15 is a partially disassembled perspective view showing a state, wherein a connector and a driving part are mounted on a lowercase of FIG. 2.
Figure 16:
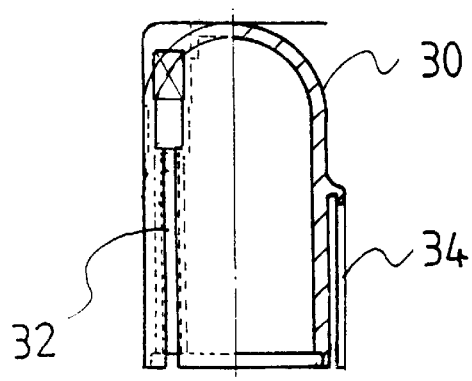
FIG. 16 is a cross sectional view, wherein a concave groove, into which a liquid hose is inserted on the uppercase, is formed

As shown in FIGS. 1, 6 and 15, the present invention has a running part 60 which includes a starting part 40. The starting part 40 prevents a driving part 50 from being separated by pressurizing a pressurized hose 53 wound on a pressurized roller 52. The pressurized roller 52 is formed on the driving roller 51 of the driving part 50 (FIG. 6). The driving part 50 which forms the driving roller 51 is rotated with a reduced rotating power. A gear for reducing the rotating force of a motor M is combined on a lower case 10. A battery holder 17 and a circuit board 600 (FIG. 19) are formed in the lower case 10. A circuit and a software program are input in the circuit board 600 to control the operation of the motor A. The running part 60 is inserted fixedly into a reception space 24 to be inserted and removed therefrom. An upper case 33, which is open and shut by hinge 300 of a cover plate 20 is also provided. The running part 60 is further designed to be driven by connecting with a liquid medicine hose 70 (FIG. 4) which is accepted in reception space 33. The running part 60 is driven while the uppercase 30 is combined to be open and shut on the lower case 10.

Figure 19:
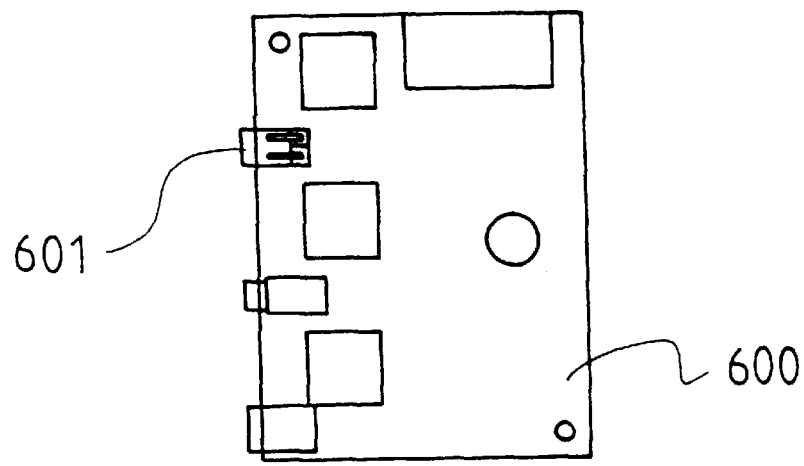
FIG. 19 is a plan view of a state, wherein a safety node is formed on a board.
Figure 20:
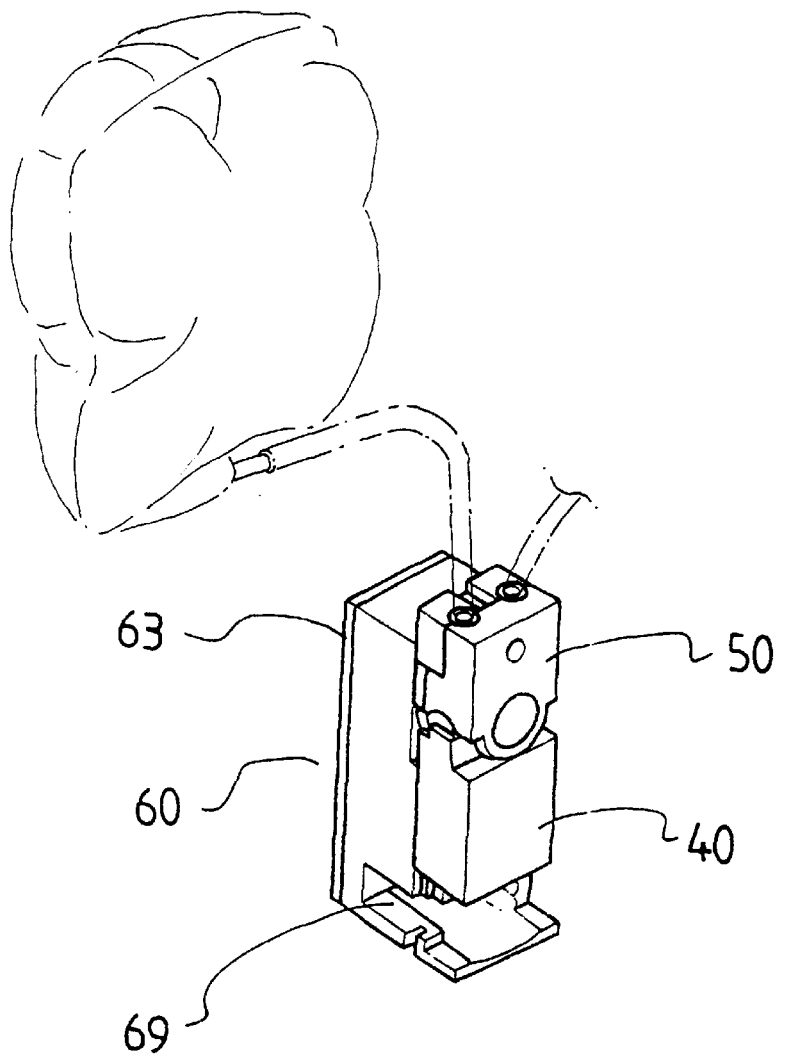
FIG. 20 is a perspective view showing an example, wherein a liquid medicine pack is connected into a driving part.
Figure 21:
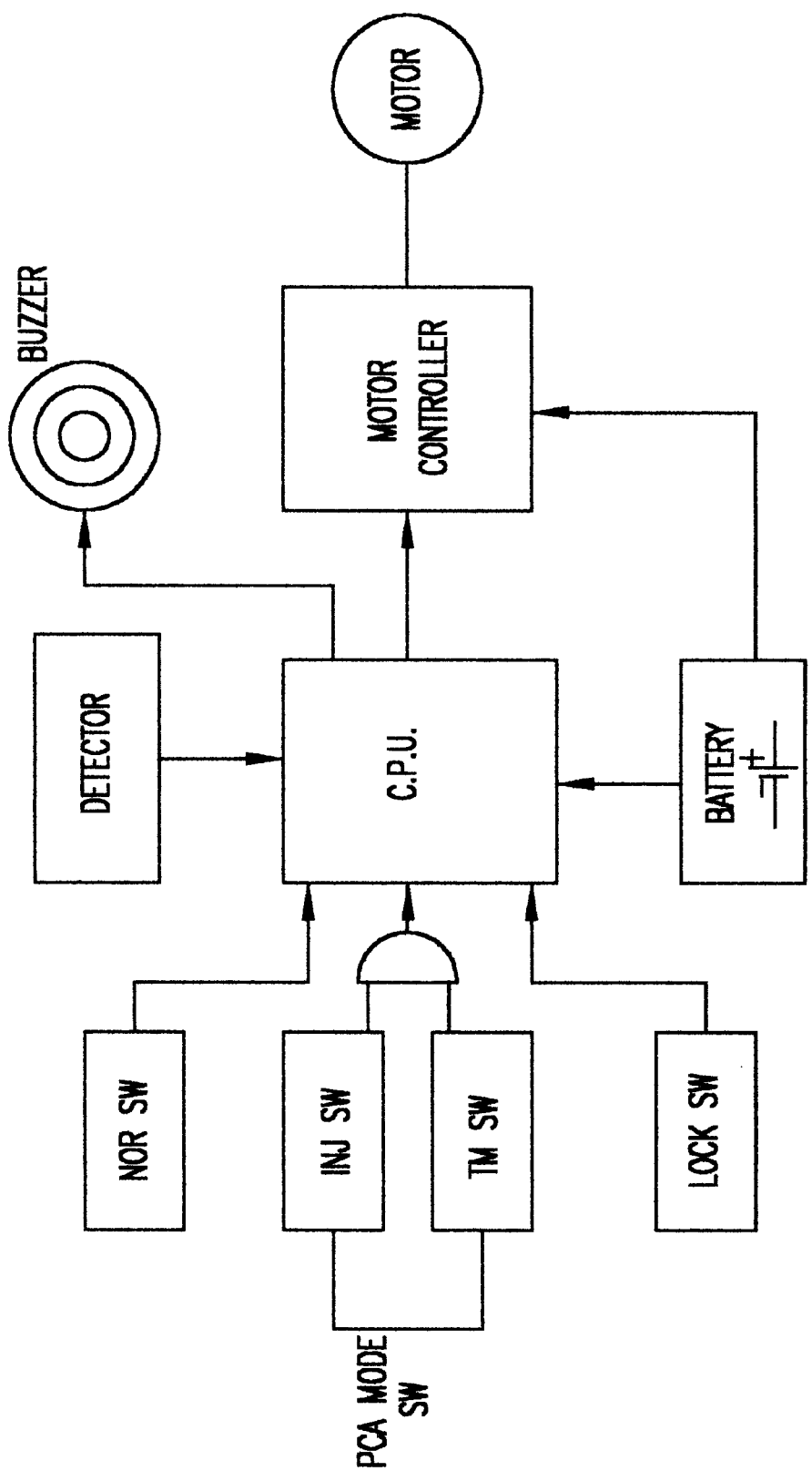
FIG. 21 is a block diagram of a working system according to an embodiment of this invention.

At this time, on the circuit board 600, as shown in FIG. 19, a safety node 601 can be inserted and removed. The safety node 600 can block the free operation of the circuit. It is also impossible to amend free operation or normal operation in the case that the safety node 601 should be removed.

Also, in order to open and shut the upper case 30 and the lower case 10, a spring 13 which is inserted into a protrusion axis 12 and pressurized by jammed plate 15 of an operation button 14 is provided. A combining protrusion 16, which is made to go in gear elastically with the combining protrusion 31 of the upper case 30, is also provided.

The cover plate 20, which is open and shut by the hinge 300, at the state that accepted the running part 60 into reception space 24 where a jammed protrusion 19 of lower case 10 is formed, forms an elastic plate 23. An inward groove 22 is combined with an outward protrusion 11 of the lower case 10 in order for the running part 60 not to be removed.

In the upper case 30 which is open and shut by the hinge 300 of the cover plate 20, a jammed part 34 is formed so that a clip 80 may be inserted into the back surface of uppercase 30. A concave groove 32 is formed so that a liquid medicine hose 70 can be inserted toward a front side.

At this time, the concave groove 32 has an enough space, through which a liquid medicine hose 70 that is connected with a connector 53a of the pressurized hose 53 (when the cover plate 20 is covered with the lower case 10) can get out into the concave groove 32 of the uppercase 30.

Also, on the lateral face 10a of the lower case 10, the circuit board 600 and LCD are mounted in an inner direction. The LCD shows liquid medicine-prescribing status. A switch SW is connected with the circuit board is also shown.

On another lateral side 10b, a battery holder 17 is formed so that a battery may be replaced at the outside. A battery node H is exposed in the inside of the lower part of a battery holder, and can be connected with the circuit board.

The combination of the lower case 10 is, as shown in FIG. 15, includes the lateral face 10a and lateral face 10b which are mated by using an inserting concave groove 500 and an inserting protrusion 400. The groove 500 and protrusion 400 are mated by being pressurized, and then fixed firmly with a screw. A screw protrusion 18 of the lateral face 10a is inserted together with a screw protrusion 18a of the other lateral face 10b.

Also, the running part 60 for feeding liquid medicine is inserted at the upper part into a slide groove 67 on the running part 60. The starting part 40 which is inelastic by a spring 41 and the curved protrusions 42 which is formed on the upper part of a starting part 40 are inserted between the protrusion bands 59, 59a while they pressurize the pressurized hose 53. The pressurized hose 53 is wound outwardly on the pressurized roller 52 of the pressurized roller 52 formed between the protrusion bands 59, 59a of the driving part 50. This arrangement prevents the driving part 50 from being removed. Also the driving part 50, in which a moving roller 51 is rotated thereon with the reduced rotating force of a motor M is fixed on the running part 60.

The configuration of the running part 60 is now described.

A motor M is accepted into a protruded lower area, into which a support plate 61 is protruded. A hole 62 is formed so that a motor axis B may be exposed. The motor axis B which is exposed into a hole 62 mates with a moving gear C. The moving gear C mates with a linked gear D. The speed of linked gear D is reduced while the driving axis 65 mates with the driving gear E in which a driving axis 65 is protruded. The moving gear C, support gear D, and driving gear E are provided in housing, and are fixed with the screw 200 on a housing through the screw hole 100 on the back side of fixed plate 63. A gear axis F is inserted for making rotation possible into the rotating concave groove 64 which is formed in the housing and a fixed plate 63. The edge of driving axis 65 in driving gear E is inserted into the axis groove 66 of the housing, exposed in a front direction, and inserted into the axis groove 55 of the moving roller 51.

At this time, in order to fix a motor M, the gears C, D, and E, which mate with a motor axis B by fixing a motor M with a screw 200 through a screw hole which is formed on the outer circumference of a hole 62 to be exposed by the insertion of a motor axis B, can be rotated in exact speed. In the back direction of the housing, after blocking it with a fixed plate 63 and front direction with a cover 68, a power connection node H for driving the motor with an opening 69 which is open in a lateral side is designed to be exposed.

Also, the driving axis 65 of the driving gear E has a cut in a lateral face which forms a cut face 65b. This communicates with a cut face 55a formed on the axis groove 55 of the moving roller 51. In this manner the driving roller 51, which is rotated simultaneously with the driving axis 65, is prevented from a slim phenomenon (e.g., a phenomenon running idle due to sliding). Also, in case the driving axis 65 is combined with the driving gear E (at time of simultaneous rotation), a screw protrusion 65a is inserted into the driving gear E, while the driving gear 65 is input under pressure. The screw protrusion 65a has a concave-convex shape which is inserted into the driving gear E. This prevents the slim phenomenon.

Also, with a spring 41 becoming elastic, a slide protrusion 44 is formed on the starting part 40 which intermits driving part 50. In this manner, the starting part 40 may not be moved up and down, and removed from the driving part 60 as the starting part 40 is inserted into the slide groove 67 of the driving part 60. The curved protrusion 42 prevents the driving part 50 from being removed as the spring 50 is placed between the protrusion band 59, 59a of the driving part 50 is formed on top. A hanging jaw 45 is formed inwardly so that a spring 41 may not be separated. Also, a support concave groove 43 is formed toward its lower part so that the lower part of the protrusion band 59 can be placed on the lower part.

The driving part 50, which accepts the moving roller 51 in which formed is an axis groove 55 having the same cut plane 55a in order to be inserted in gear with the cut face 65b of a driving axis 65, includes two bodies 50a, 50b. A protrusion plate 57, in which an inserting hole 56 is punched, is formed so that on the body 50a of a lateral side may be inserted a pressurized hose 53, into which a connector 53 is inserted in the lateral edge, to be fixed. In the case of being combined with another side of body 50b, the protrusion plate 57 is made to be placed on the lower part of an insetting groove 54. In the lateral side of the protrusion plate 57, the extended partition 58 is formed and in another lateral face, a partition 58 with which a space 57a is made, is formed so that another side edge of a pressurized hose 53 may be inserted. Thus, the pressurized hose 53, which is wound externally on the side of a pressurized roller 52, is exposed toward the outside.

At this time, the cut groove 50c is formed on the upper of the lateral face in the body 50a and is inserted to be combined into the inserting protrusion 60a of the driving part 60.

The pressurized hose 53, which is wound on the pressurized roller 52 (which is inserted with a pin G in order to make a moving roller 51 rotate), is combined with a connector 53a, 53b. This structure is stuck to the pressurized roller 52 so that it may hang on an inserting groove 54 of the driving part 50. The pressurized hose 53, when stuck to the pressurized roller 52 is pressurized by a curved protrusion 42 of the starting part 40.

With the moving roller 51 placed between the protrusion bands 59, 59a, a curved protrusion 42 of the starting part 40 pressurizes only the pressurized hose 53 which is wound on the pressurized roller 52 of the moving roller 51.

The protrusion band 59a of the lateral body 50a forms a jaw 59b and has a hole. A moving roller 51 is protected, with the other side of a body 50b being blocked. The jaw of the fixed plate 51b engages a gear to be combined with each other on a jaw 59b, which is formed on a protrusion band 59b of a side body 50a. Also in the case that two bodies 50a, 50b are combined with a screw, a moving roller 51 can not be removed between protrusion band 59, 59a.

Figure 12:
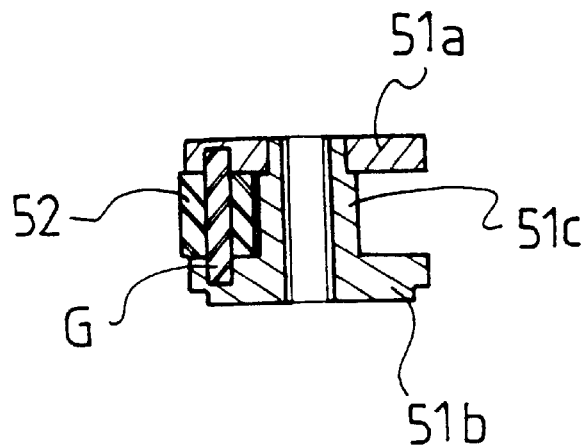
FIG. 12 is a cross sectional view showing a state, wherein the pressurizing roller of a driving roller is mounted.
Figure 13:
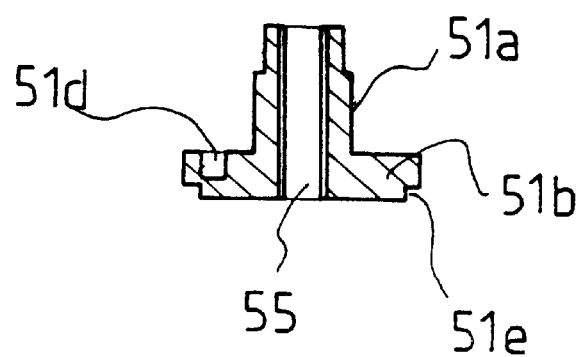
FIG. 13 is a cross sectional view of a fixed plate of a driving roller.
Figure 14:
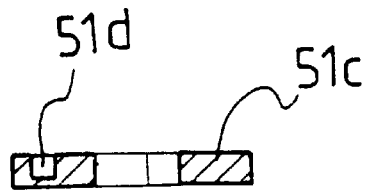
FIG. 14 is a cross sectional view of a cover plate of a driving roller.

As shown in FIG. 12 and FIG. 14, the pressurized roller 52 is combined with the pin G is shown. This shown arrangement prevents the pin G from being removed. Specifically, a fixed plate 51b, on which a protrusion axis 51a is formed, is designed to be combined with a cover plate 51c. A concave groove 51d is formed toward the inside of the cover plate 51c and the fixed plate 51b. A pin G is inserted into the concave groove 51d between the cover plate 51c and the fixed plate 51b. A pressurized roller 52 is then inserted into a pin G.

In the methods of the cover plate 51c being combined with the protrusion axis 51a of the fixed plate 51b, there are both a method of pressurizing and a method of blending, mounting and adhesion. In these methods, a cut face 55a is formed at the center of the protrusion axis 51a, the axis groove 55.

Figure 3:
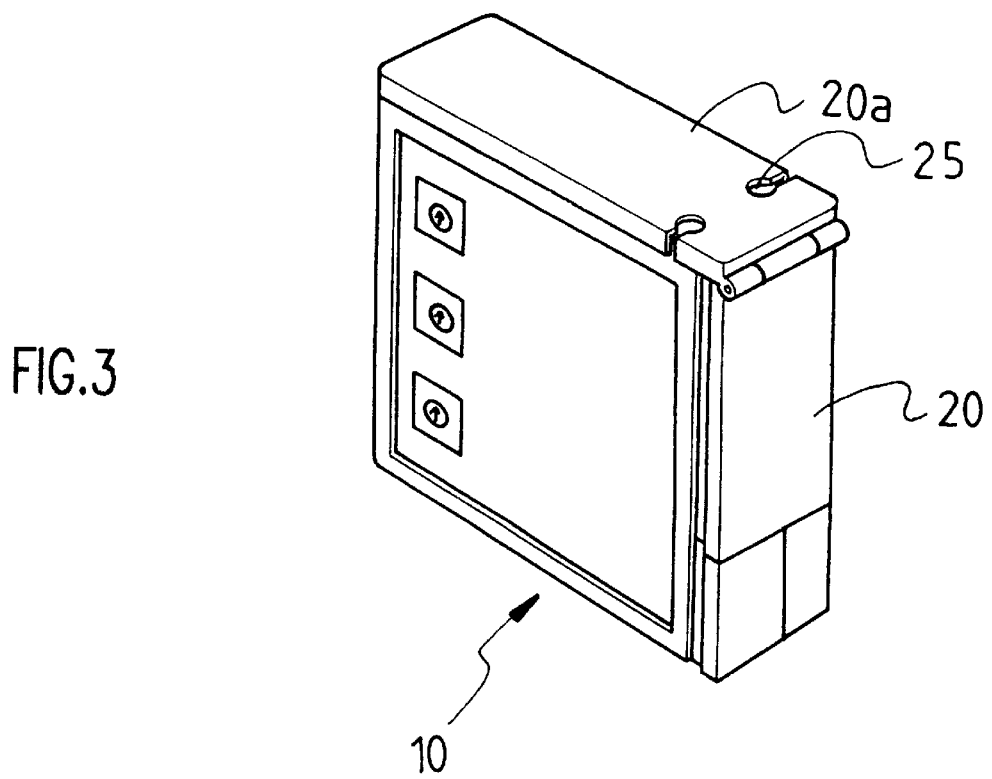
FIG. 3 is a perspective view showing a state, wherein there is no uppercase.
Figure 5:
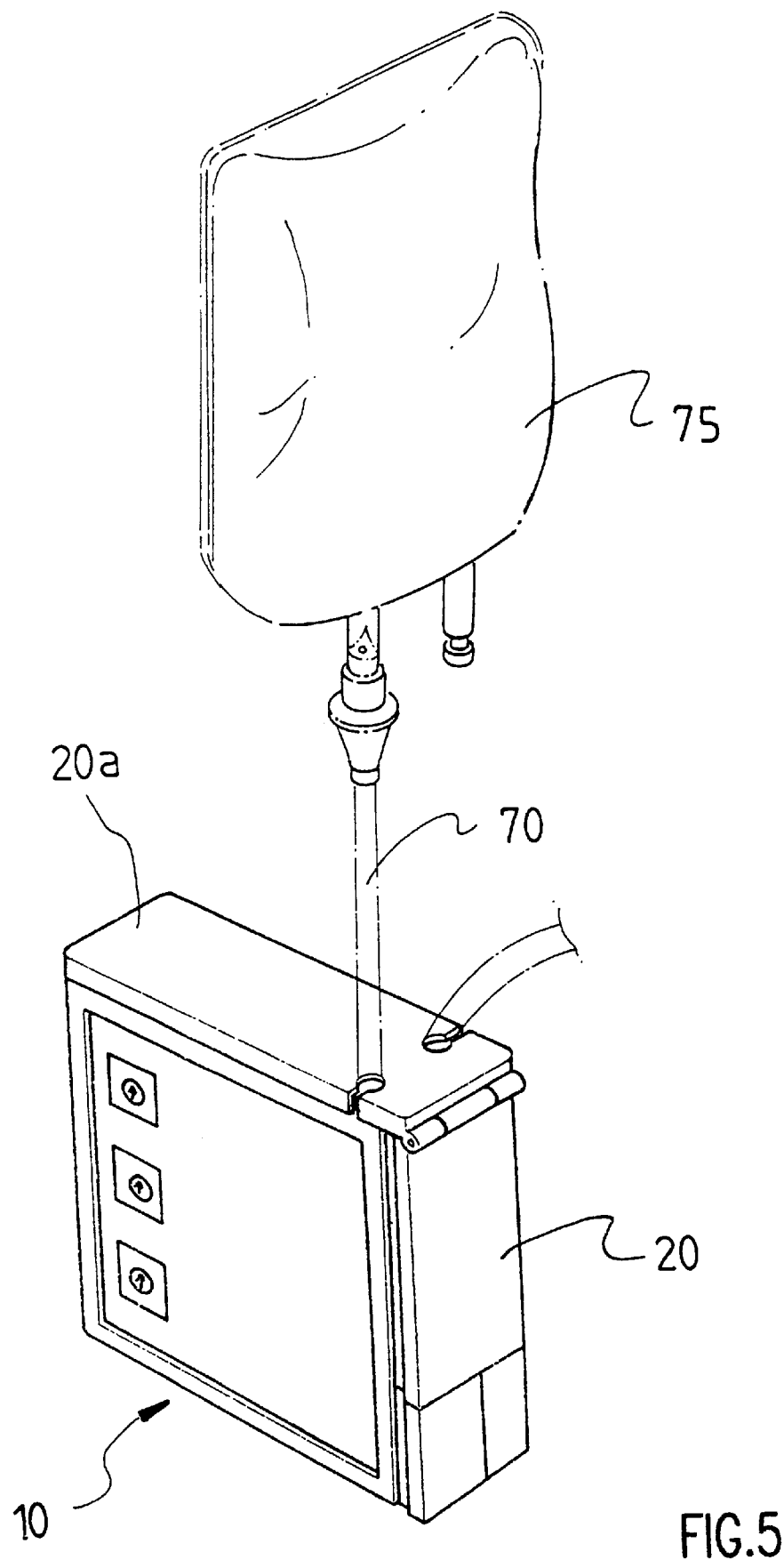
FIG. 5 is a perspective view showing a state, wherein a liquid medicine pack is connected without the uppercase.
Figure 17:
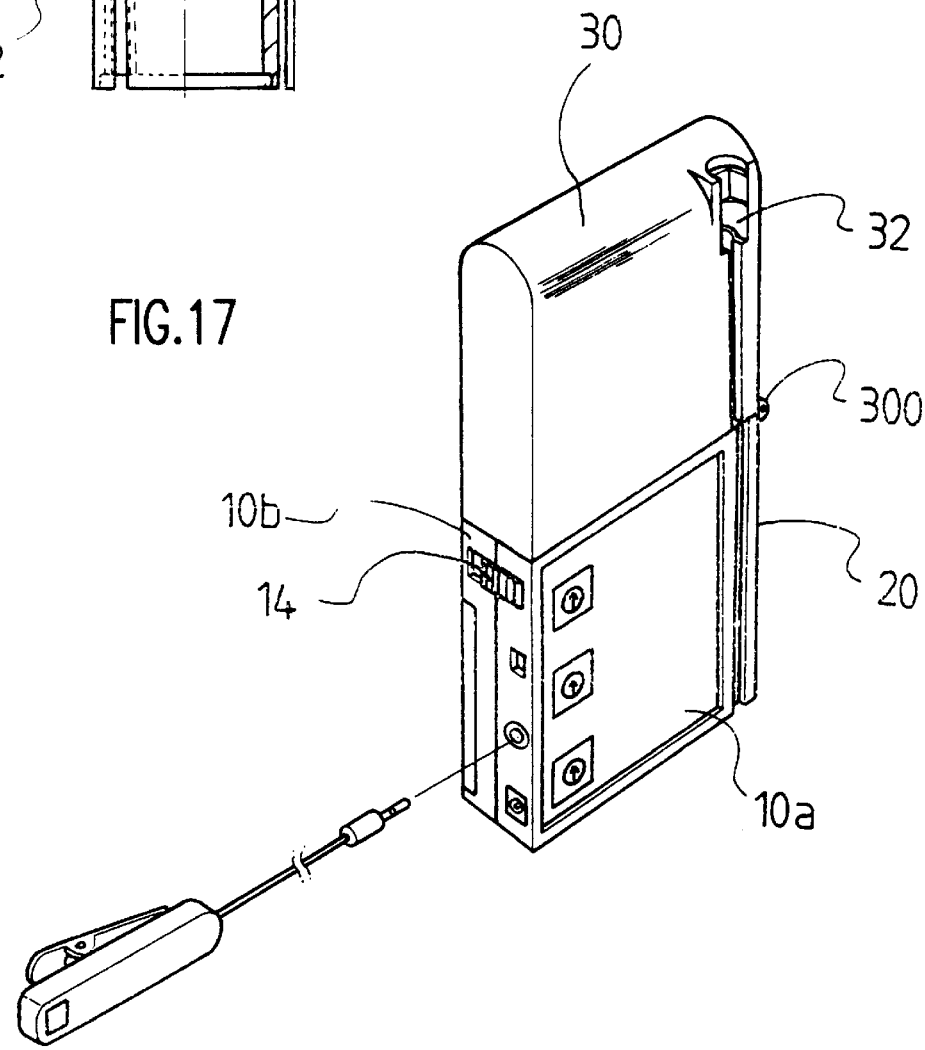
FIG. 17 is a perspective view showing a state, wherein a remote controller is formed to be used.
Figure 18:
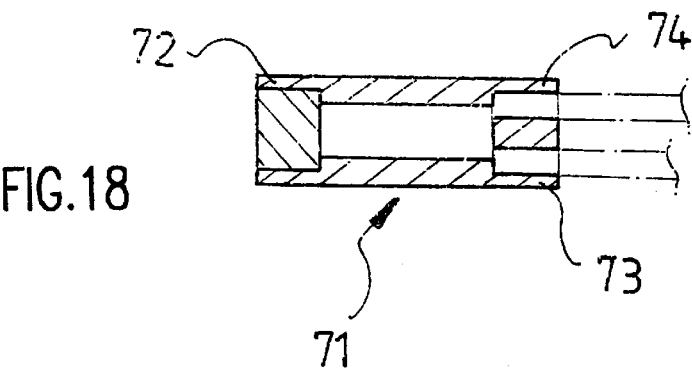
FIG. 18 is a cross sectional view of a connector.

Also, without the upper case 30 and the lower case 10 being folded and unfolded by a hinge 300, as shown in FIG. 15, by protruding the combing protrusion 90 toward the top of the lower case 10, the combining protrusion 90 is combined in the upper case 30. As shown in FIG. 3 and FIG. 5, by forming the lower case 10 without the uppercase 30, in the direction crossing directly over the cover plate 20 which is folded and unfolded by the hinge (it is not shown in the drawing) into the top of the lower case 10, another cover plate 20a, which is folded and unfolded by the hinge 300, is formed. By forming the hole 25 which can expose a liquid medicine hose into the top of the above cover plate 20a, various applications can be achieved. Also, as seen in FIG. 17, a remote controller can be connected.

As shown in FIG. 15, after forming a guide groove 10c in the lateral face 10b of the lower case 10 and after inserting the safety pin 10d through the above guide groove 10, the safety pin 10d is placed between the supporting concave groove 43 of the starting part 40 and the protrusion band 59 of the driving part 50 for preventing the pressurized hose 23 from being pressed before using the goods.

Accordingly, in the case that the driving part 60 should be made on the lower case 10, if pushing an operation button 14, mounted on the lower case 10, toward a lateral side, the jammed plate 15 pressurizes the spring 13 and the combining protrusion 31 of the uppercase 30, which engages the protrusion 16, is separated. This opens the uppercase 30. At the state that the uppercase 30 is open, if pressurizing the elastic plate 23 of the cover plate 20, the inward groove 22 of the elastic plate 23 is removed from the outward protrusion 16 of the lower case 10 and the cover plate 20 is open and a reception space 24 is exposed, so after accepting the running part 60 into the reception space 24, in which an inserting protrusion 19 is formed, by using a node H which is exposed into the lower area of a running part, it is connected with a circuit board 600.

At the above connected state, after accepting the liquid medicine pack into the reception space 33 of the uppercase 30, the liquid medicine hose 70, which is connected with the liquid medicine pack, is designed to be connected with a side of the connector 53a of the pressurizing hose 53 which is exposed into the top of the driving part 50. In another side, the hose 71 is made to be connected with the injection needle in order to inject into blood vessel by using the liquid medicine hose.

After that, if pausing a switch SW as the motor A starts driving, and since the moving roller 51 is inserted into the driving axis 65 of the driving gear E, the pressurized roller 52 of the moving roller 51 is rotated simultaneously with the roller 51. At the state that the pressurized hose 53 which adheres closely to the pressurized roller 52 begin to be pressurized at regular intervals by the pressurized roller 52, and the liquid medicine, which is filled in the liquid medicine bottle or the liquid medicine pack which is connected with the pressurized hose 53, flows in a side according to the liquid medicine hose 70.

Figure 2:
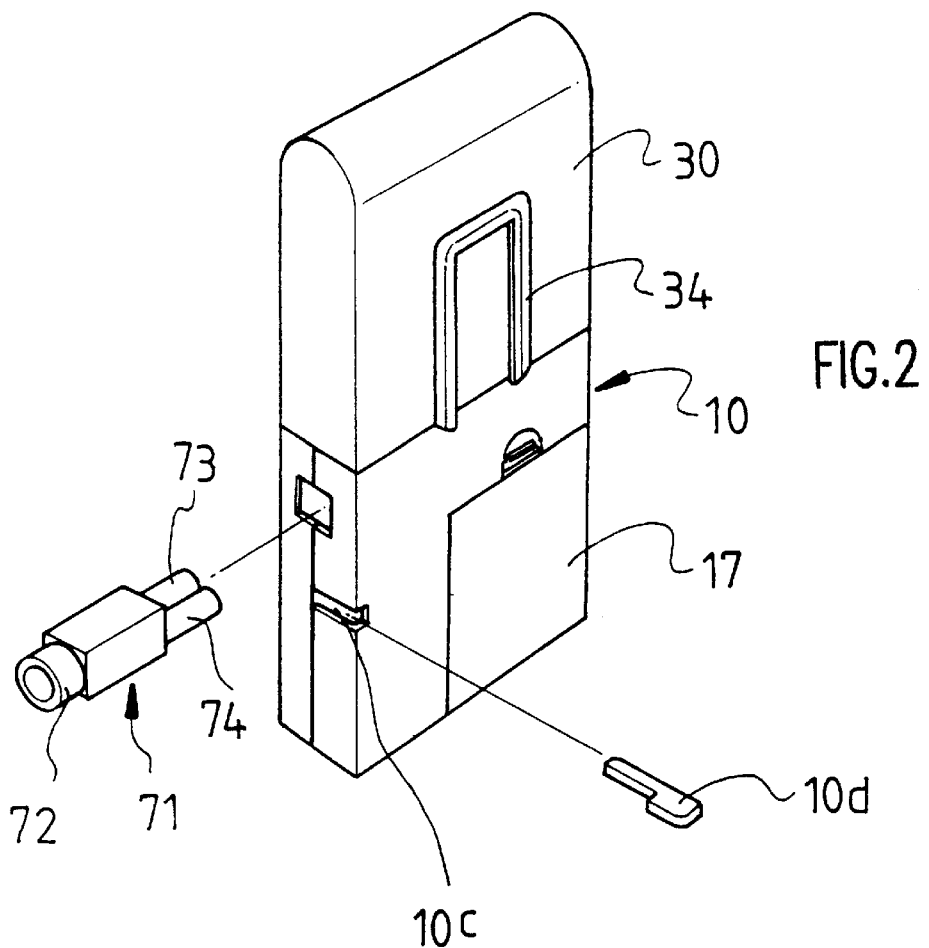
FIG. 2 is a perspective view showing a state, wherein uppercase is fixed on lowercase.

FIG. 2 shows the upper case 30 fixed on the lower case 10. In order to pour the liquid medicine into the liquid medicine pack when the liquid medicine pack is accepted into the reception part 33 of the upper case 30 connecter 71 is provided. The connector 71 branches off into two branches 73, 74 and an inlet 72 which is exposed into the outside of the connector 71 (FIG. 15). The liquid medicine flows through the inlet 72 if a liquid medicine is injected by using an injection needle through the inlet 72 of the connector 71. The branch 73 is connected with the liquid medicine pack and the other branch 74 is connected with the pressurized hose 53. Since the pressurized hose is pressurized by a curved protrusion 42 formed on the top of the starting part 40, liquid medicine is prevented from flowing into the branch 74 and flows only into the liquid medicine pack 75 through a branch of a side.

At this time, the pressurized hose connected with the branch 74 of another side is connected with a patient's blood vessel by being connected with an injection needle for injection through the liquid medicine hose 70. Since a silicon rubber is inserted into the inlet 72 of the connector 71, air is shut off in the case that an injection needle comes in and out.

Accordingly, by using this principle, various applications are possible, for example, (i) at the state that the liquid medicine pack is accepted into the reception part 33 of the upper case 30 or (ii) without the upper case 30 at the state that the liquid medicine is exposed in the outside, or (iii) in the case that slow injection is required by being connected with an injection needle, or (iv) in the case of the disposable use or in the case of the recharging use. In the case of the disposable use, since the driving part 50 is removed from the starting part 40, it is possible to replace only the driving part 50 and use it again.

In the case that the running part 60 is to be replaced, easy replacement is possible by opening the cover plate 20, separating the node H of the motor A from the circuit board, and removing the running part 60. In the case that only the pressurized hose 53 of the driving part 50 is to be replaced, the starting part (which is elastic and is supported with a spring if lowering the starting part 40 downward) goes down and the curved protrusion 42 of the starting part 40 is moved from between the protrusion band 59, 59a of the moving roller 51. Also, if the moving part 50 is separated from the driving axis 65, the pressurized hose 53 which is wound on the pressurized roller 52 of the moving roller 51 can be easily replaced by separating the body 50a, 50b of the moving part 50.

Accordingly, at the separated state, if the moving part 50 which includes two bodies 50a, 50b is to be separated, the pressurized hose 53 which is wound on the external side of the pressurized roller 52 of the moving roller 51 can be removed. After removing, a new pressurized hose 53 can be connected in use.

Also, operation is by driving of a motor M by applying an electric power due to the conversion of a personal conversion PCA MODE switch SW and a normal conversion switch SW which are formed outwardly in the lower case 10. This is because the motor, which is connected with a circuit board, is controlled by the circuit which is arranged on the circuit board. This driving performs automatic operation by free operation with changed value for increasing a prescribing amount freely in addition to normal operation which is done by a reference value.

Figure 22:
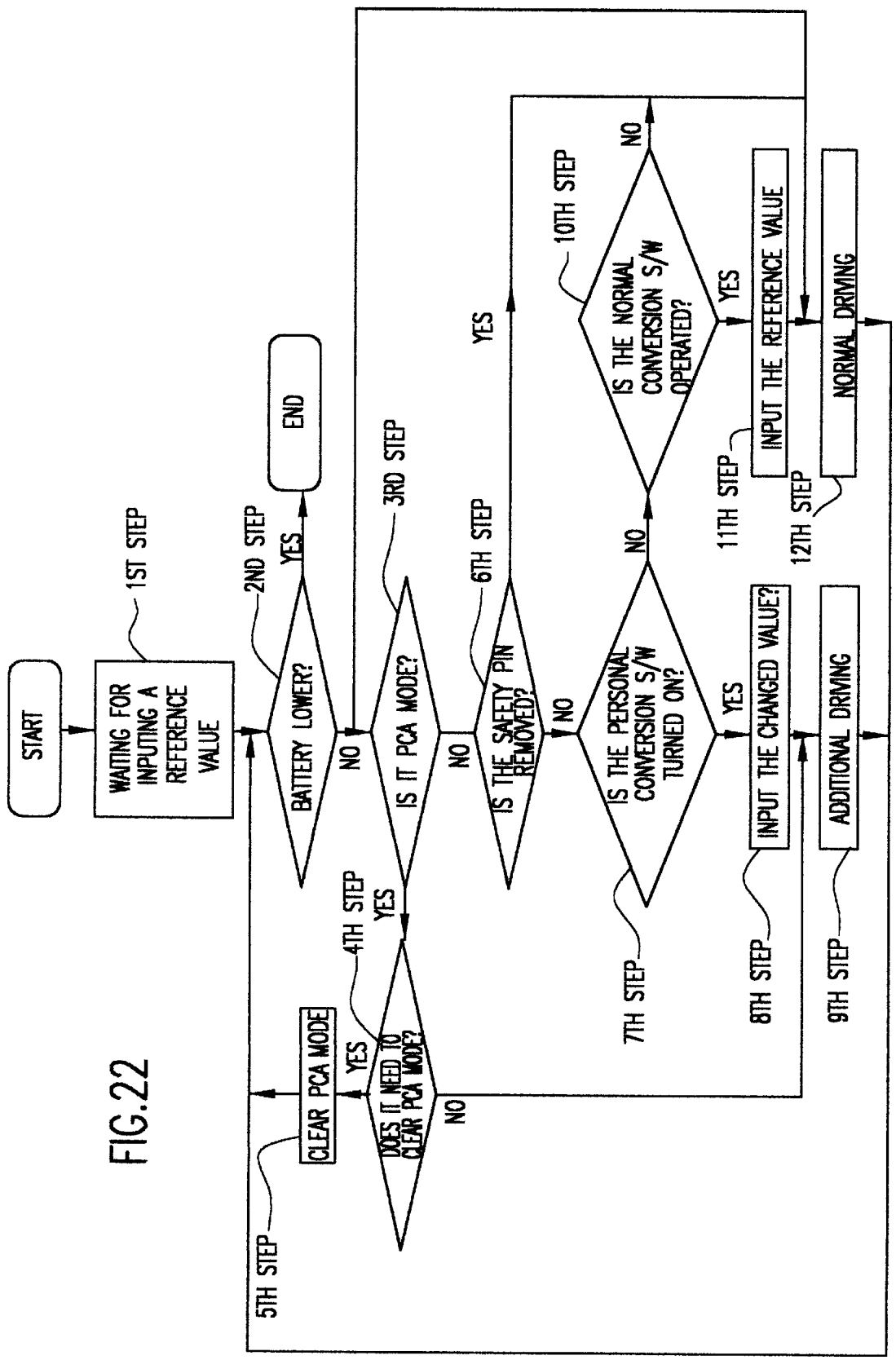
FIG. 22 is a flow chart showing the control operation of this invention.

Accordingly, in the central processing unit C.P.U., as shown in FIG. 22, if an electric power is applied by a normal conversion switch, the step goes into the first step which detects the applying of an electric power in the central processing unit, makes clear a changed value and a reference value stored in memory for normal operation and free operation in advance. After passing the first step which stands by a new input state, the second step determines the appropriateness of a battery. If the battery is not proper to use, all the operations are ended. If appropriate, the step goes into the third step which determines whether a personal conversion switch is working or not (whether it is PCA mode or not) with which a patient can freely add to the prescribing amount of liquid medicine. If it is set in PCA mode, the step goes into the fourth step which determines whether the PCA mode which is previously input should be cleared or not. If it should not be cleared, the step goes into the ninth step which is operated at the free operation which is previously input and in the case that it is required to be cleared, the step goes into the fifth step which makes clear the PCA mode, which is previously input.

As the above, in the case that PCA mode is cleared at the fifth step, after passing through the second and the third steps, the step goes into the sixth step which confirms the safety pin-removing state. If the safety pin was removed (that is to determine whether a safety node is off in order for a patient to make free operation impossible about the increase of liquid medicine), the step goes into the twelfth step which is operated normally according to a reference value. If the safety pin is not removed, the step goes into the seventh step which determines whether PCA switch is newly working. If the PCA switch is not working (that is, when the capacity and the time of a personal conversion switch are not pressurized at the same time or turned off), the step goes into tenth step which determines whether the reference switch for normal operation was changed or not. If not changed, the step goes into the eleventh step which is working normally according to the reference value. If the normal conversion switch was changed according to the reference value, the step goes into the eleventh step which is operated by the reference value which was changed by normal conversion switch and the twelfth step which is normally operated.

Also, at the seventh step, if the PCA switch turns on (that is, when, in a personal conversion switch, a prescribing amount-determining switch and a prescribing time-determining switch as well are pressurized at the same time), the step goes into the eighth step which starts the working of free operation at the time the normal operation comes to an end in PCA mode. If free operation is working, the normal operation does not work during the time which is previously set and the amount which is freely prescribed. And, after free operation, if free operation is finished, free operation is changed into normal operation.

Also, the normal operation according to the reference value performs rotation for a constant time which is input with a reference value at intervals of thirty seconds by the reference value input from the normal conversion switch which is divided into nine steps. For the remaining time, the normal operation performs the stop operation for the motor. The changed value in PCA mode, which is input simultaneously with the prescribing time switch and the prescribing amount switch, is designed to be free operation so that the prescribing amount may be prescribed additionally at intervals of the prescribed time by dividing the prescribing time switch and the prescribing amount switch into nine steps respectively. These operations are effective only for one time and, in the case of free operation, normal operation is suspended.

Figure 24:
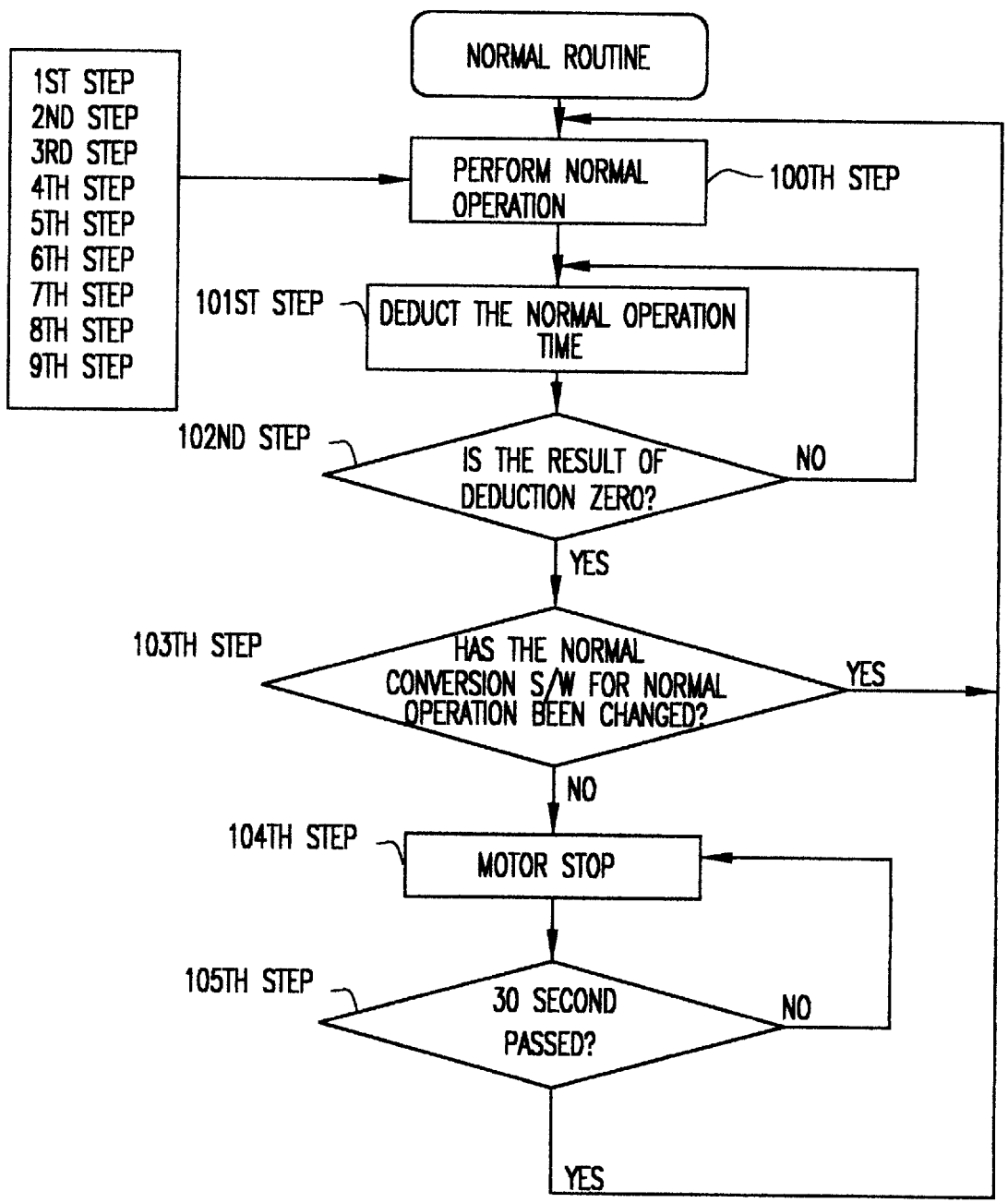
FIG. 24 is a subroutine view of a normal conversion mode (NOR mode) shown in FIG. 21.

Accordingly, the routine for normal operation is controlled as shown in FIG. 24.

In the routine in the case of normal operation, since the reference value of the first step is set as 250 ms if the normal conversion switch which is divided into nine steps is set the same as the first step, the motor performs normal operation according to the 100th step immediately and deducts the normal operation time according to a reference value from the 101st step. At this time the time interval which is counted is designed to be counted per 10 ms and 50 ms.

Accordingly, the motor M which is normally operated by the 100th and the 101st steps go into the 102nd step which determines whether the value is zero or not as a result of deduction. If the value does not reach zero, the step goes into a circulating loop which alternates the 101st step with the 100th step, so repeated operation is made. If the value reaches zero, the step goes into the 103rd step which determines whether a normal conversion switch for normal operation has been changed or not. If it was changed, the step goes into the 100th step which is working immediately at the state that was changed. If it was not changed, the step goes into the 104th which makes the motor stop.

After that, in case that 30 seconds have not passed after being operated at the 105th step, the 104th step repeats with the 105th step and forms a circulating loop in which a motor continues to stop. In the case that 30 seconds are passed, the step goes into the 100th step, so normal operation is performed.

At this time, in this invention, the driving time of a motor is set to be 30 seconds, but according to the characteristic of liquid medicine which should be prescribed, it can be adjusted. As for the counting time, in this invention, it is set to be 10 ms and 50 ms units for counting time, but it also can be adjusted according to use condition.

That is, since a normal conversion switch is divided into nine steps, if rotating it into the ist step from OFF state, immediately after that, the motor M is rotated. Also, since at this time, the reference value of the motor M for rotation is set to be 250 ms at the 1st state, the motor M can be rotated for 250 ms which is a reference value. For the remaining time of 29.75, the motor stops.

Also, the PCA mode which is freely operated by the personal conversion switch, contrary to the repetitive driving at the normal operation, operation is effective only once. For example, in the case that the motor M is rotated by normal operation, if the mode is changed into PCA mode at the state that the motor stops or is being rotated, normal operation is performed only for 250 ms set at the normal operation state. After that, at the state that the mode is changed into PCA mode, normal operation stops during one time operation and in the case that PCA mode is canceled, normal operation is performed immediately.

Figure 23A:
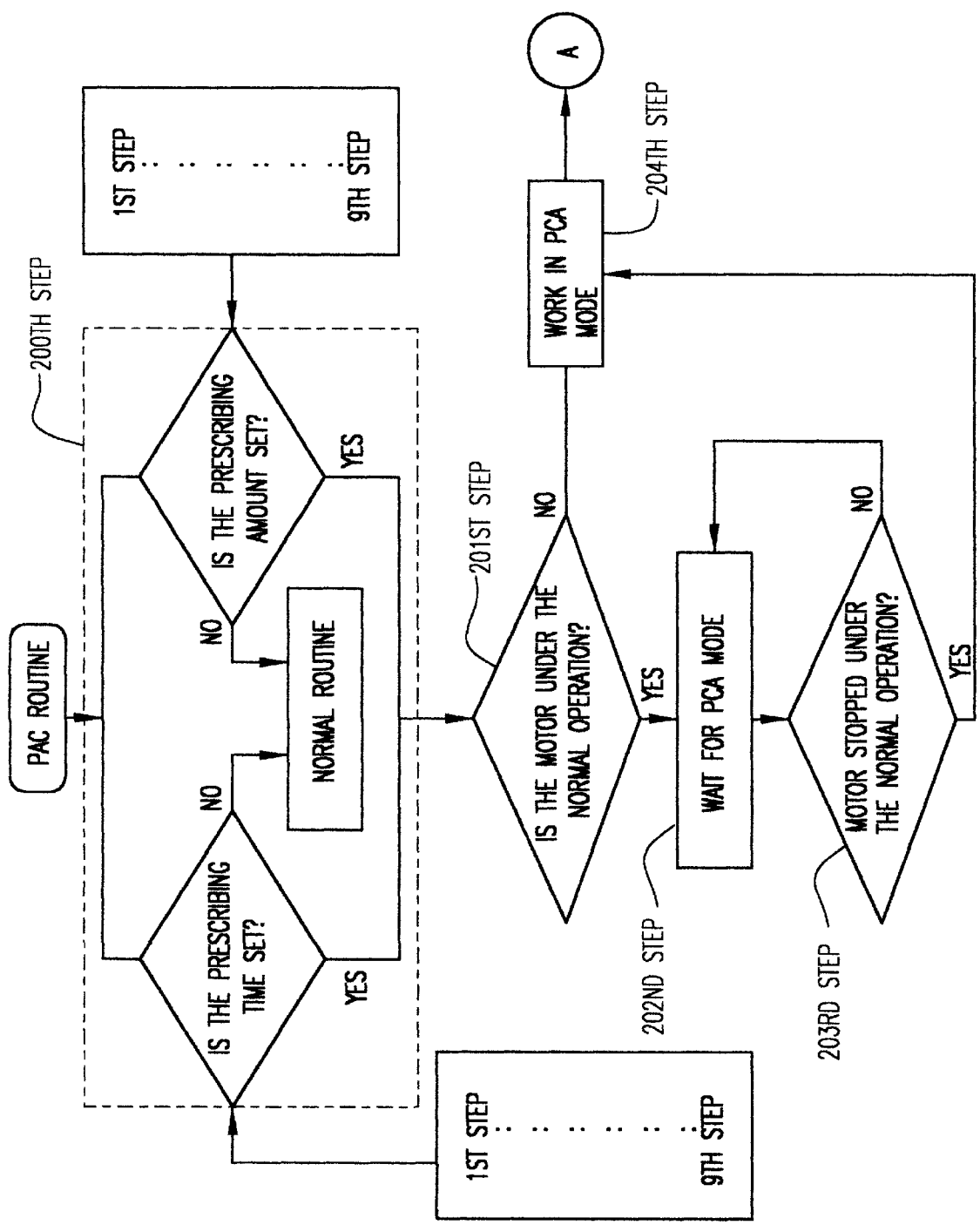
FIGS. 23A and 23B are a subroutine view of a personal conversion mode (PCA mode) shown in FIG. 21.
Figure 23B:
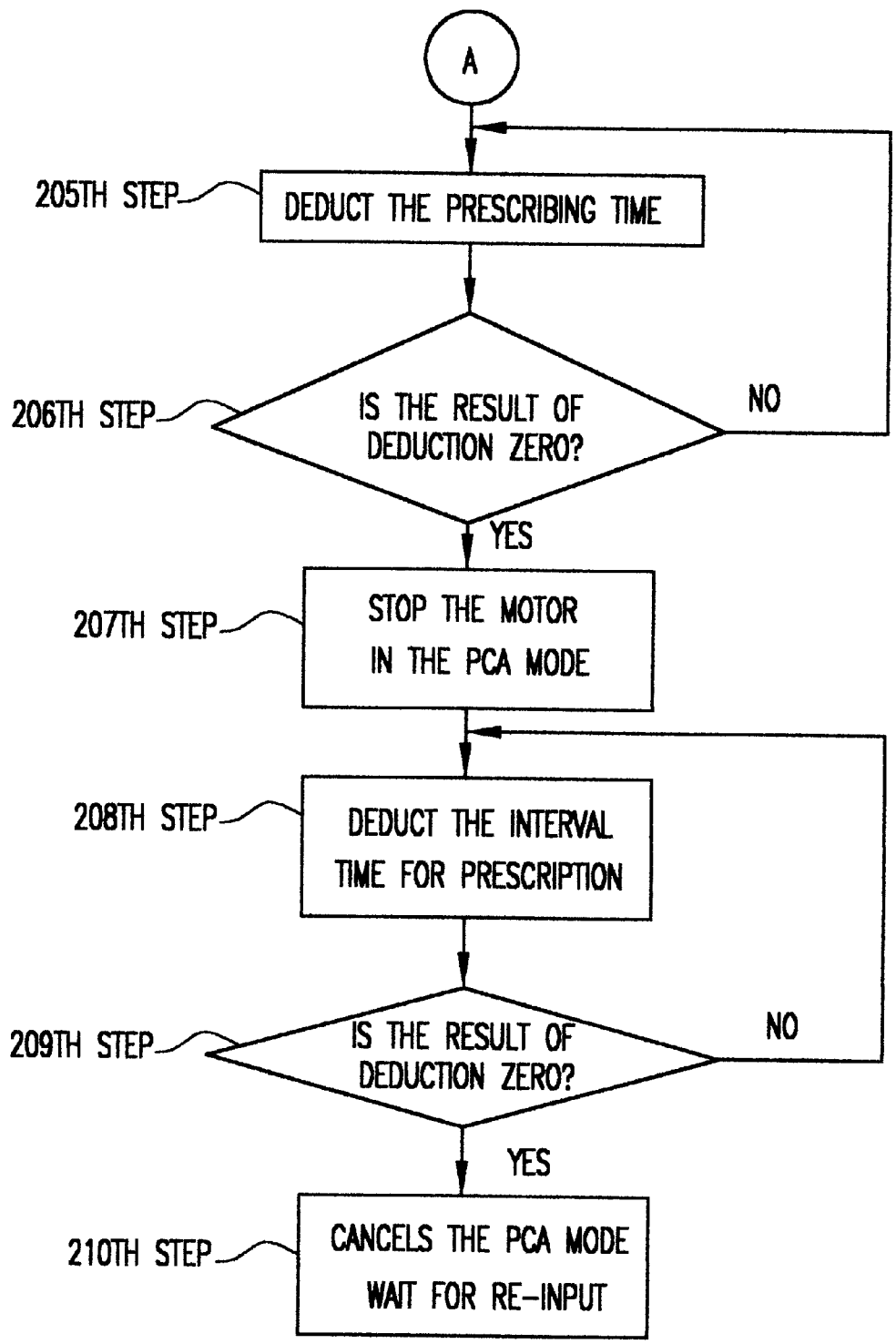

The PCA mode routine for this is the same as FIG. 23.

In order to work in the PCA mode and in order to operate only when the changed value of the prescribing interval time and the changed value of the prescribing amount, which are classified into nine steps respectively, are input simultaneously, at the 200th step which determines whether the changed value of the prescribing amount and the prescribing time are input simultaneously by the prescribing amount and the prescribing time input. If input is not done simultaneously, PCA mode is not working, but is working in normal operation state. If input is done simultaneously, at the 201st step which determines whether a motor for normal operation is being rotated before working in PCA mode. If a motor is being rotated, PCA mode is in a waiting state at the 202nd step. At the waiting state, (e.g., at the state which determines whether the rotating motor is stopped or not) if the motor is being rotated, the step goes into the 202nd step. This is a circulating loop. If the motor stopped, the step goes into the 204th step, thus performing the PCA mode immediately.

Also, in the case that the motor is not rotated at the 201st step, the step goes into the 204th step immediately to be performed in PCA mode.

If operation begins, the time value according to the prescribing amount at the 206th step is deducted and, whether the result of deduction became zero is determined. If not zero at the 206th step, the step goes into the 205th which forms a circulating loop and the motor continues to be driven. If it became zero, the step goes into the 207th step in which the operation of the motor stops in the PCA mode. If the motor stops, the step goes into the 208th step, in which the changed value of the prescribed interval time is deducted.

After that, the step goes into 209th step which determines whether the result of deduction for the prescribing interval time became zero. If it did not become zero, the step goes into the 208th step which forms a circulating loop. If it became zero, the step goes into 210th step which cancels PCA mode and immediate normal operation is performed.

Also, in the case that PCA mode is working, even in the case that, for the second time, operation is made to be performed in PCA mode, operation is made to stop. That is to say, only when PCA mode is canceled, a new input signal can be accepted.

At this time, the motor is rotated for the time for the prescribing amount the same as normal operation and the motor stops during the remaining time which deducts the time for the prescribing amount, e.g., the prescribing interval time.

Accordingly, as the motor M is rotated continuously, the pressurized roller of the moving roller does not pressurize the pressurized hose continuously, but operation is working during the time for the value given within the constant range of time. Thus, not only the expected life span of the motor can be extended, but also a battery life can be extended. Also, in order for the patient to increase the prescribing amount, a fixed quantity can be prescribed by the use of a button.

This invention having the above configuration is disposable and is a portable liquid medicine-supplying apparatus with which a patient can take directly for portable use by putting on it while walking. Also, it is possible for a patient to use it over and over again according to multiple injection only for the patient who has to use the same liquid medicine.

Also, this invention not only minimizes the causes which interfere with daily life, but also increases the effectiveness according to the medical treatment of liquid medicine. This invention has another benefit in that a fixed quantity of liquid medicine is input as well as the prescribing amount of the liquid medicine can be adjusted for a patient to maintain good health. That is to say, this invention offers an extensive prescribing range.

Accordingly, this invention offers the features such as the convenience of its use, good liquid medicine-prescribing speed, no error in the liquid medicine-prescribing amount due to outside temperature change, safety and reliability, and no maintenance fee is required.

It will be apparent to those skilled in the art that various modifications can be made in The liquid medicine-prescribing apparatus for blood vessel injection of the present invention, without departing from the spirit of the invention. Thus, it is intended that the present invention cover such modifications as well as changes thereof, within the scope of the appended claims and their equivalents.

What is claimed is:

1. A liquid medicine-prescribing apparatus for a blood vessel injection comprising;
    a lower case having two lateral faces,
    a running part having feed means of liquid medicine;
    a cover plate mounted to one of the two lateral faces of the lower case by a first hinge on a first edge of the cover plate;
    a reception space for holding the running part, the reception space being formed by the cover plate and the two lateral faces of the lower case which is open and shut by a hinge 300 of lowercase 10; and
    an upper case which is open and shut by a second hinge located between the upper case and a second edge of the cover plate,
    wherein the upper case and the cover plate form a second reception space adapted to hold a liquid medicine pack.

2. The liquid medicine-prescribing apparatus for a blood vessel injection according to claim 1, further comprising a second cover plate which includes a hole punched toward an upper side of the lower case, the second cover plate being openable by a third hinge located between the second cover plate and the cover plate.

3. The liquid medicine-prescribing apparatus for blood vessel injection according to claim 1, further comprising:
    an inlet provided in the lower case;
    a connector having two branches branching off from the inlet; and
    a protrusion extending from one of the two lateral faces of the lower case and adapted for combining the upper case and the lower case.

4. The liquid medicine-prescribing apparatus for a blood vessel injection according to claim 1, further comprising:
    a spring;
    a protrusion axis positioned on one of the two lateral faces of the lower case and accommodating the spring;
    a jam plate positioned at an end of the spring;
    an operation button extending beyond the jam plate;
    a combining protrusion positioned proximate to the jam plate and the operation button; and
    an upper case protrusion contacting the combining protrusion when the upper case is in a closed position,
    wherein the spring, the operation button, the combining protrusion and the upper case protrusion are adapted for opening and closing the upper case and the lower case.

5. The liquid medicine-prescribing apparatus for a blood vessel injection according to claim 1, further comprising:
    a guide groove in one lateral face of the lower case;
    a starting part mounted to the running part;
    a driving part mounted to the running part and proximate to the starting part;
    a supporting concave groove formed in the starting part;
    a protrusion band positioned partly about the driving part;
    a safety pin inserted through the guide groove and between the supporting concave groove and the protrusion band for preventing a pressurized hose from being pressed prior to dispensing of medicine.

6. The liquid medicine-prescribing apparatus for a blood vessel injection according to claim 1, further comprising:

an elastic plate having an inward groove formed on the cover plate; and an outward protrusion formed on the lower case and engaging the inward groove when the lower case is in a closed position, wherein the running part positioned within the reception space is prevented from being removed when the lower case is in the closed position.

7. The liquid medicine-prescribing apparatus for a blood vessel injection according to claim 1, further comprising:

a jammed part formed in the upper case; and a concave groove formed in the upper case on a side opposing the jammed part, wherein a clip is adapted to be inserted into a back surface of the upper case and a liquid medicine hose is adapted to be inserted within the concave groove such that the liquid medicine hose can be inserted toward a front side of the upper case.

8. The liquid medicine-prescribing apparatus for a blood vessel injection according to claim 1, further comprising:

a slide groove formed on an upper portion of the running part for holding a starting part;

a spring positioned between the starting part and the running part;

curved protrusions formed at an upper part of the starting part;

protrusion bands communicating with the curved protrusions and which pressurize a pressurized hose;

a driving part having a pressurized roller 52 of a pressurized roller and a moving roller, the pressurized roller being formed between the protrusion bands for preventing the driving part from being removed, the moving roller rotates with a reduced rotating force of a motor M which is fixed on the running part.

9. The liquid medicine-prescribing apparatus for a blood vessel injection according to claim 1, wherein the two lateral faces of the lower case are combined with a screw such that a screw protrusion of one lateral face is inserted together with a screw protrusion of another lateral face of the two lateral faces.

10. The liquid medicine-prescribing apparatus for a blood vessel injection according to claim 8, further comprising:

a support plate protruding from the lower area of the running part and supporting the spring, the motor being positioned below the support plate;

a hole formed in the running part so that a motor axis B can be exposed therethrough, the motor axis B meshing with a driving gear;

a linking gear having a gear axis;

a driving gear having a driving axis communicating with the linking gear, the speed of the linking gear being reduced when the driving axis communicates with the motor M ;

a housing for housing the moving gear, the linking gear and the driving gear, the housing including a fixed plate, a screw hole and a concave groove, the gear axis being inserted within the concave groove of the fixed plate thereby allowing rotation of the gear axis;

an edge of the driving axis being inserted into an axis groove of the housing, exposed toward a front direction, and inserted into an axis groove of the moving roller.

11. The liquid medicine-prescribing apparatus for a blood vessel injection according to claim 8, further comprising:

a slide protrusion formed on the starting part 40;

a hanging jaw formed inwardly of the starting part thereby preventing the spring from being separated therefrom; and a support concave groove formed below the curved protrusions.

12. The liquid medicine-prescribing apparatus for a blood vessel injection according to claim 10, further comprising:

an axis groove having a cut plane formed on the driving part and insertable into a cut face of the driving axis;

a protrusion plate having an inserting hole formed near the curved protrusions and accommodating a pressurized hose;

the protrusion plate being positioned in a lower part of an insetting groove;

an extended partition formed in a first lateral face of the protrusion plate; and a second extended partition is formed in another lateral face of the protrusion plate, the second extended partition having a space so that the pressurized hose may be inserted therethrough and wound externally on a side of the pressurized roller and exposed toward an outside of the housing.

13. The liquid medicine-prescribing apparatus for a blood vessel injection according to claim 10, further comprising a power connection node H for driving the motor and extending through an opening positioned below the support plate.

14. The liquid medicine-prescribing apparatus for a blood vessel injection according to claim 10, wherein:

the driving axis of the driving gear includes a cut face which communicates with an axis groove of the moving roller such that when the moving roller is rotated simultaneously with the driving axis a slim phenomenon is prevented; and the driving axis combined with the driving gear at time of the rotation further prevents the slim phenomenon by forming a screw protrusion having a concave-convex shape on a part inserted into the driving gear and opposing the cut face.

15. The liquid medicine-prescribing apparatus for a blood vessel injection according to claim 10, further comprising:

a pin communicating with the pressurized roller and allowing the moving roller to be rotated;

connectors formed in both ends of the pressurized hose; and an inserting groove formed on the driving part for holding the pressurized hose which is wound about the pressurized roller and which is pressurized by the curved protrusions.

16. The liquid medicine-prescribing apparatus for a blood vessel injection according to claim 12, further comprising:

a jaw having a hole formed on one of the protrusion bands;

a fixed plate holding the moving roller;

a jaw formed on the fixed plate, the jaw of the fixed plate being combined with a jaw formed on the one protrusion band; and the moving roller capable of being removed between the protrusion bands.

17. The liquid medicine-prescribing apparatus for a blood vessel injection according to claim 12, further comprising:

a pin for holding the moving roller on a fixed plate;

a cover plate having a concave groove formed on an inner part of the cover plate, the cover plate positioned on an opposing side of the moving roller with respect to the fixed plate; and a second pin being inserted into the concave groove between the cover plate and the fixed plate, the pressurized roller being inserted into the second pin.

18. The liquid medicine-prescribing apparatus according to claim 12, wherein an incising groove is formed on top of a body of of the running part and is combined to be fixed by being inserted into an inserting protrusion of the running part.

19. The liquid medicine-prescribing apparatus for a blood vessel injection according to claim 3, further comprising:

a guide groove in one lateral face of the lower case;

a starting part mounted to the running part;

a driving part mounted to the running part and proximate to the starting part;

a supporting concave groove formed in the starting part;

a protrusion band positioned partly about the driving part;

a safety pin inserted through the guide groove and between the supporting concave groove 43 of a starting part 40 and the protrusion band for preventing a pressurized hose from being pressed prior to dispensing of medicine.

20. The liquid medicine-prescribing apparatus for a blood vessel injection according to claim 2, further comprising:

a jammed protrusion provided in the lower case;

an elastic plate having an inward groove formed on the cover plate; and an outward protrusion formed on the lower case and engaging the inward groove when the lower case is in a closed position, wherein the running part positioned within the reception space is preventing from being removed when the lower case is in the closed position.

21. The liquid medicine-prescribing apparatus for a blood vessel injection according to claim 3, further comprising:

a jammed part formed in the upper case; and a concave groove formed in the upper case on a side opposing the jammed part, wherein a clip may be inserted into a back surface of the upper case and a liquid medicine hose can be inserted within the concave groove can be inserted toward a front side of the upper case.

22. The liquid medicine-prescribing apparatus for a blood vessel injection according to claim 2, wherein the two lateral faces of the lower case are combined with a screw such that a screw protrusion of one lateral face is inserted together with a screw protrusion of another lateral face of the two lateral faces.

23. The liquid medicine-prescribing apparatus for a blood vessel injection according to claim 3, wherein the two lateral faces of the lower case are combined with a screw such that a screw protrusion of one lateral face is inserted together with a screw protrusion of another lateral face of the two lateral faces.

24. The liquid medicine-prescribing apparatus for a blood vessel injection according to claim 1, wherein the first edge for mounting the first hinge is perpendicular to the second edge for mounting the second hinge.

\* \* \* \* \*